United States Patent
Finch et al.

(10) Patent No.: US 6,299,610 B1
(45) Date of Patent: Oct. 9, 2001

(54) METHODS AND APPARATUS FOR DISINFECTING SUBCUTANEOUSLY IMPLANTED DEVICES

(75) Inventors: Charles D. Finch, Clinton; Jeffrey H. Burbank, Boxford; James M. Brugger, Newburyport; John H. Wang, North Andover, all of MA (US)

(73) Assignee: Vasca, Inc., Tewksbury, MA (US)

( * ) Notice: Subject to any disclaimer, the term of this patent is extended or adjusted under 35 U.S.C. 154(b) by 0 days.

(21) Appl. No.: 09/003,772

(22) Filed: Jan. 7, 1998

(51) Int. Cl.[7] .................................................. A61M 31/00
(52) U.S. Cl. ........................ 604/506; 604/500; 604/93.01
(58) Field of Search ............................ 604/93, 264, 280, 604/175, 8, 190, 180, 252, 48, 500, 506, 514, 518, 265

(56) References Cited

U.S. PATENT DOCUMENTS

| | | |
|---|---|---|
| 4,573,994 | 3/1986 | Fischell et al. . |
| 4,579,554 | 4/1986 | Glassman . |
| 4,767,411 | 8/1988 | Edmunds . |
| 4,959,054 | 9/1990 | Heimke et al. . |
| 5,004,455 | 4/1991 | Greenwood et al. . |
| 5,185,003 | * 2/1993 | Brethauer ................................ 604/93 |
| 5,236,422 | 8/1993 | Eplett, Jr. . |
| 5,261,896 | 11/1993 | Conway et al. . |
| 5,263,930 | 11/1993 | Ensminger . |
| 5,308,338 | * 5/1994 | Helfrich ................................ 604/175 |
| 5,482,740 | 1/1996 | Conway et al. . |
| 5,591,145 | 1/1997 | Sachse . |
| 5,599,321 | 2/1997 | Conway et al. . |

OTHER PUBLICATIONS

Hemasite II® Product Brochure, Renal Systems, Inc., 14905 28th Avenue North, Minneapolis, MN, 55441, USA, Telephone: 1-800-328-3340, 14 pages total.

* cited by examiner

*Primary Examiner*—Manuel Mendez
*Assistant Examiner*—Kent Gring
(74) *Attorney, Agent, or Firm*—Townsend and Townsend and Crew LLP

(57) ABSTRACT

Implantable ports and other devices are disinfected by the injection of an anti-microbial agent into a tissue pocket surrounding the device. In a first embodiment, the anti-microbial agent is injected through an aperture in the device to flush internal regions of the device before infusing the tissue pocket. In other embodiments, the anti-microbial agent is injected directly to a target site on the exterior of the device. Implantable devices may include special, usually hardened, target regions for receiving the sharpened end of a needle used to inject the anti-microbial agent.

37 Claims, 4 Drawing Sheets

US 6,299,610 B1

METHODS AND APPARATUS FOR DISINFECTING SUBCUTANEOUSLY IMPLANTED DEVICES

BACKGROUND OF THE INVENTION

1. Field of the Invention

The present invention relates generally to medical devices and methods. More particularly, the present invention relates to methods for disinfecting implanted devices and to modified devices which facilitate such disinfection methods.

Subcutaneously and transcutaneously implanted devices are utilized for a wide variety of purposes. Heart pacemakers have become commonplace. Transvascular catheters are used for a variety of purposes, including hemodialysis access, drug infusion, and the like. Of particular interest to the present invention, subcutaneously and transcutaneously implanted ports and catheters have been proposed for both drug infusion and hemodialysis access. All such implanted devices are subject to infection of surrounding tissue pockets. Subcutaneously implanted ports which are periodically accessed by needles and other percutaneously introduced devices are particularly subject to infections introduced by the access device.

Heretofore, infections of subcutaneously implanted devices have usually been treated by administering antibiotics to the patient after infection has become established. Most often, the implanted device must also be removed and replaced, subjecting the patient to additional trauma and leaving the patient without benefit of the device for the time it takes to clear the infection and replace the device. Moreover, the need to administer antibiotics periodically to patients is expensive and patients who suffer from repeated infections often become resistant to particular antibiotics.

As an alternative to antibiotic treatment and/or device removal, U.S. Pat. No. 5,263,930 proposes to provide a disinfectant reservoir in an implantable vascular access port. The reservoir includes a septum to permit periodic replenishment with a suitable anti-microbial agent. Agent introduced into the reservoir flows into an access lumen through the device. Catheters and other devices inserted into the access lumen become coated with the anti-microbial agent to provide a barrier against infection along the percutaneous access route. While potentially beneficial, the provision of a static volume of anti-microbial agent within a reservoir does not provide flushing and active decontamination of the tissue pocket surrounding the implanted port. Thus, should bacteria be introduced into the tissue pocket, it is unlikely that the anti-microbial agent would be effective to inhibit infection.

For these reasons, it would be desirable to provide improved methods and devices for inhibiting bacterial and other infections in subcutaneously implanted devices. It would be particularly desirable to provide methods and devices for active flushing of the implanted device as well as the tissue pockets and regions surrounding the device in order to maximize the disinfection process. It would be particularly useful if such methods and devices were applicable not only to implantable ports but also to other subcutaneously and transcutaneously implanted devices. At least some of these objectives will be met by the present invention as described hereinafter.

2. Description of the Background Art

U.S. Pat. No. 5,263,930 has been described above. A transcutaneous vascular access port sold under the tradename HEMASITE® II by Renal Systems, Inc., Minneapolis, Minn., includes an above-skin reservoir for a bactericide, as described in a brochure entitled Vascular Access System copyrighted by the manufacturer in 1984. Catheters having bacteriocidal coatings and release capabilities are described in U.S. Pat. Nos. 5,599,321; 5,591,145; 5,482,740; 5,261,896; 5,236,422; 5,004,455; 4,959,054; 4,767,411; and 4,579,554.

SUMMARY OF THE INVENTION

The present invention provides methods and improved apparatus for inhibiting infection of subcutaneously and transcutaneously implanted devices. The methods and apparatus are particularly applicable to disinfection of implanted vascular and other access ports which are at substantial risk of infection through repeated percutaneous access via needles, access cannulas, stylets, and the like. The present invention, however, will also be useful with a variety of other subcutaneously implanted devices, including pacemakers, catheters, prosthetic joints, defibrillators, implantable infusion pumps, and the like.

The present invention relies on percutaneous injection of an anti-microbial agent in an amount sufficient to infuse a region surrounding the device within a pocket of tissue. The anti-microbial agent may be any one of a variety of conventional bactericidal, fungicidal, virucidal, or other disinfecting agents, typically being selected from the group consisting of sodium hypochlorite, calcium hypochlorite, sodium oxychlorosone, alcohols, aldehydes, halides, providone iodine, peroxides, and the like. The agent will usually be in the form of a liquid, although it could also be a flowable gel, and will usually be injected at a volume in the range from about 0.05 ml to 50 ml, often from 1 ml to 50 ml, more often from 2 ml to 25 ml, and typically from 2 ml to 10 ml. Injection will conveniently be effected using a needle which can be penetrated directly through the skin, typically in combination with a conventional syringe.

In a preferred aspect of the method of the present invention, the subcutaneously implanted device is a port which is connected to a blood vessel, other body lumen or cavity, or solid tissue target site, usually using a cannula. The port has an aperture for receiving a percutaneous access tube, e.g. a needle. The anti-microbial agent is injected directly into the aperture to both flush the aperture and any internal volume surrounding or in fluid communication with the aperture, with excess anti-microbial agent being flushed from the aperture to infuse a region or space surrounding the port within the tissue pocket in which the port has been implanted. Usually, the port will be valved to isolate the access aperture from that portion of the port which is connected to the cannula and/or the blood vessel or body lumen. Thus, flushing of the port with the anti-microbial agent can be performed without introduction of the agent beyond the valve, i.e. into the blood vessel or other target site. The needle used to flush the access port will be introduced in a manner which does not open the valve structure, thus maintaining isolation. The needle used to introduced the anti-microbial agent, however, will usually be introduced through the same site or tissue tract as the primary access tube, thus reducing patient trauma. The disinfecting needle will usually be smaller than the access tube, even further reducing patient trauma.

The methods of the present invention are also useful for disinfecting and inhibiting infection with ports and other subcutaneously implanted devices which do not have open access apertures. In such cases, it will usually be unnecessary to disinfect internal portions of the device, and the disinfecting needle can be contacted directly against an external surface of the device in order to infuse the anti-microbial agent within the tissue pocket surrounding the device. Optionally, the needle may be contacted against a specially configured target site on the device, e.g. a well or other region on the device composed of or lined with a relatively hard material that can withstand repeated contact with the disinfecting needle. The well or other target can be located by the treating professional, e.g. by manually feeling it through the skin, and will be positioned to permit the anti-microbial agent to infuse freely about the exterior of the device at the interface between the device and the tissue. In some cases, it may be desirable to connect the well to channels or other surface features which permit the anti-microbial agent to suffuse freely around the periphery of the device.

In yet another embodiment, the methods may be used to disinfect transcutaneously implanted devices, such as catheters. In such cases, the disinfectant is infused into the tissue pocket formed about the device, usually by injection into tissue through a location adjacent to device penetration site. As with previous embodiments, the disinfectant is able to suffuse and flush the tissue pocket, and the excess disinfectant will flow outward around the device onto the patient's skin, to assure thorough disinfection.

The present invention further provides improved implantable devices of the type which include a housing implanted within a subcutaneous tissue pocket. The improvements comprise a non-penetrable target site on the housing for receiving a disinfecting needle to permit delivery of an anti-microbial agent as described above. Preferably, the non-penetrable target site is composed of or lined with a metal or other material which is sufficiently hard to withstand repeated engagement by the disinfecting needle. Suitable materials include metals, such as titanium, vanadium, stainless steel (particularly 316L), as well as implant grade plastics and ceramics. The well may have a circular geometry, an annular geometry, or may be connected to a network of channels or wells which facilitate distribution of the anti-microbial agent about the device implanted within the tissue pocket.

DESCRIPTION OF THE SPECIFIC EMBODIMENTS

The present invention provides novel methods for disinfecting subcutaneously and transcutaneously implanted devices subject to such infection. The methods rely on injecting a suitable anti-microbial agent into a region or regions within a subcutaneous pocket into which the device has been previously implanted. optionally, the anti-microbial agent will be injected through an aperture in order to flush internal spaces within the device, where excess anti-microbial agent will then suffuse outwardly through the same aperture and infuse into the tissue pocket. Alternatively, the anti-microbial agent may be injected directly onto a target site on the exterior of the device. Modified devices according to the present invention will include a special target site configured to facilitate aiming of the needle and/or infusion of the anti-microbial agent about the device.

The anti-microbial agent will comprise one or more active components selected to kill or inactivate pathogens of a type which infect subcutaneously and transcutaneously implanted devices. Suitable active agents include bactericides, fungicides, virucides, and the like. Exemplary anti-microbial agents are selected from the group consisting of sodium hypochlorite, calcium hypochlorite, sodium oxychlorosone, alcohols, aldehydes, halides, providone iodine, peroxides, and the like.

The anti-microbial agent is usually in a liquid form, e.g. where the active agent is dissolved or suspended in a physiologically acceptable liquid, such as saline, sterile water, Ringer's solution, or the like. Alternatively, the anti-microbial agent may be in the form of a gel, emulsion, suspension, paste, powder, or other injectable fluid or material of a type normally employed in pharmaceutical uses.

The anti-microbial agent will be injected in an amount sufficient to infuse at least a portion of the interstitial space surrounding the subcutaneously or transcutaneously implanted device, referred to herein as the "tissue pocket." Usually, the volume of anti-microbial agent injected will be sufficient to infuse through the entire tissue pockets surrounding device. When injected only on the exterior, the volume will usually be at the lower end of the ranges set forth above, e.g. from 0.05 ml to 10 ml. Often, however, in cases where internal portions of the device are also being flushed, the volume will usually be greater, i.e. being sufficient to completely fill and flush the internal regions as well as having sufficient access to infuse through at least a portion, and preferably all, of the tissue pocket. Preferably, the volume will be sufficient to further express outwardly from the tissue pocket through the needle puncture site to flush potentially infecting organisms away from the implanted device and tissue tract. Such volumes will be in the range from 1 ml to 50 ml. In the case of implanted access ports, the volume will typically be in the range from 1 ml to 25 ml, more usually from 3 ml to 10 ml.

Figure 1:
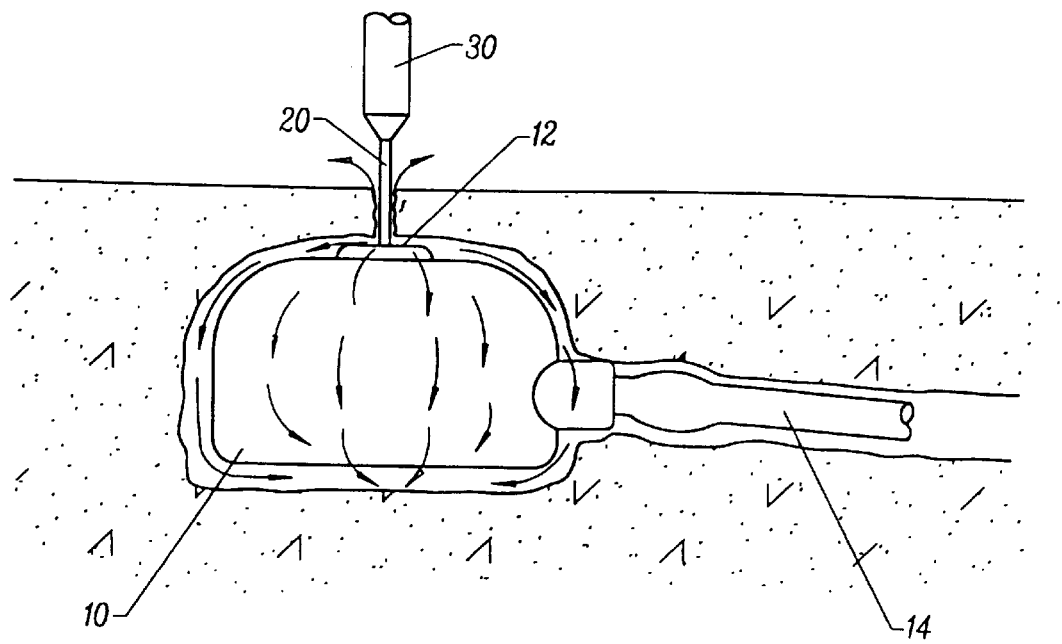
FIG. 1 illustrates an implanted vascular port having an access aperture being disinfected according to the method of the present invention.
Figure 2:
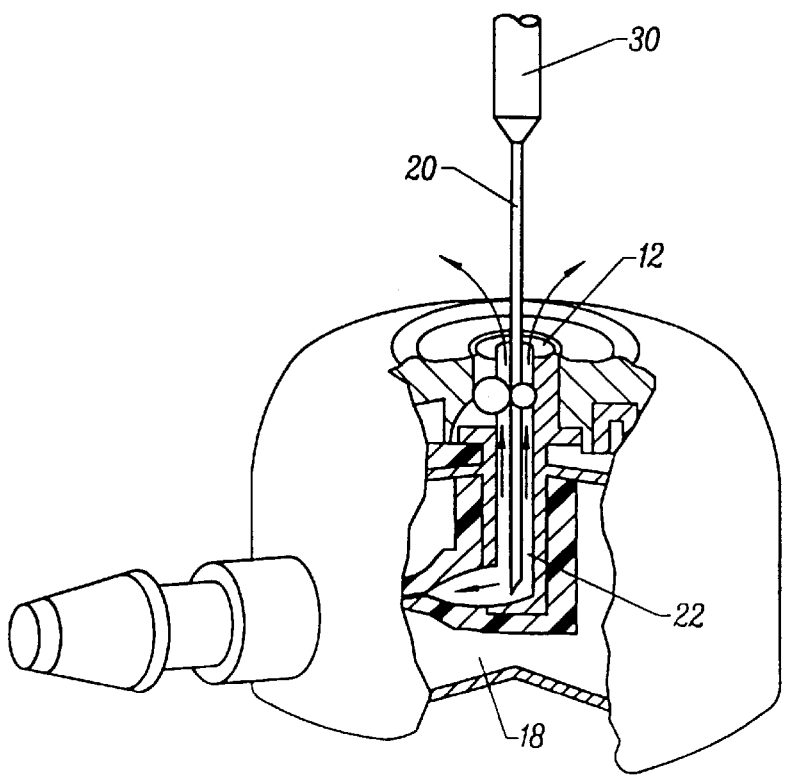
FIG. 2 is a detailed view of the port of FIG. 1, with portions broken away, illustrating the flow of anti-microbial agent within the internal regions of the port.

Referring to FIGS. 1 and 2, a first exemplary method according to the present invention will be described. A subcutaneously implanted port 10 is of the type which includes an aperture 12 for receiving a percutaneously introduced access tube (not shown), of the type described in co-pending application Ser. No. 08/857,386, filed on May 15, 1997, assigned to the assignee of the present invention, the full disclosure of which is incorporated herein by reference. In normal use, the access tube is introduced through the aperture 12 and a fluid is transferred between the access tube and an implanted cannula 14, which may be connected to a blood vessel, the peritoneal cavity, or other target site within the patient. The port 10 further comprises a valve structure 18, where the valve is normally closed, i.e. closed in the absence of the access tube. For the purposes of the present invention, the details of the valve mechanism 18 are unimportant. It is important only that the valve is actuated when a relatively large access tube is introduced through the aperture 12, e.g. a fourteen gauge access tube in the case of the specific port 10 described in the co-pending application.

Disinfection of the port 10 is accomplished using a needle 20 which is smaller than the access tube which is normally used to access the port. For example, a twenty-five gauge needle 20 may be introduced through the aperture 12 and substantially to the bottom of a vertical access path 22, as best seen in FIG. 2. The needle encounters a metal surface at the bottom of the access path 22, so the valve structure 18 is not damaged. Introduction of the smaller needle 20 does not actuate the valve mechanism, so the valve 18 remains closed, isolating the aperture 12 and access path 22 from the cannula 14.

After the needle 20 is in place, as shown in FIGS. 1 and 2, the anti-microbial agent may be injected using a syringe assembly 30 connected to the needle 20, in a conventional manner. Valve ports 10 of the type described in the co-pending application, a volume of anti-microbial agent in the range from 3 mm to 10 mm has been found to be sufficient to both flush the access path 22 and associated interior volumes of the port as well as flush about the exterior of the port, as shown by the arrows in FIG. 1. The injection of anti-microbial agent may be performed before access with an access tube, after access with an access tube, or at any other time. A particular advantage of the method illustrated in FIGS. 1 and 2 lies in the fact that no additional tissue access tract needs to be formed in order to introduce the anti-microbial agent. That is, the needle 20 may be introduced through the normal tissue tract which is formed in order to access the port with the access tube.

Figure 3:
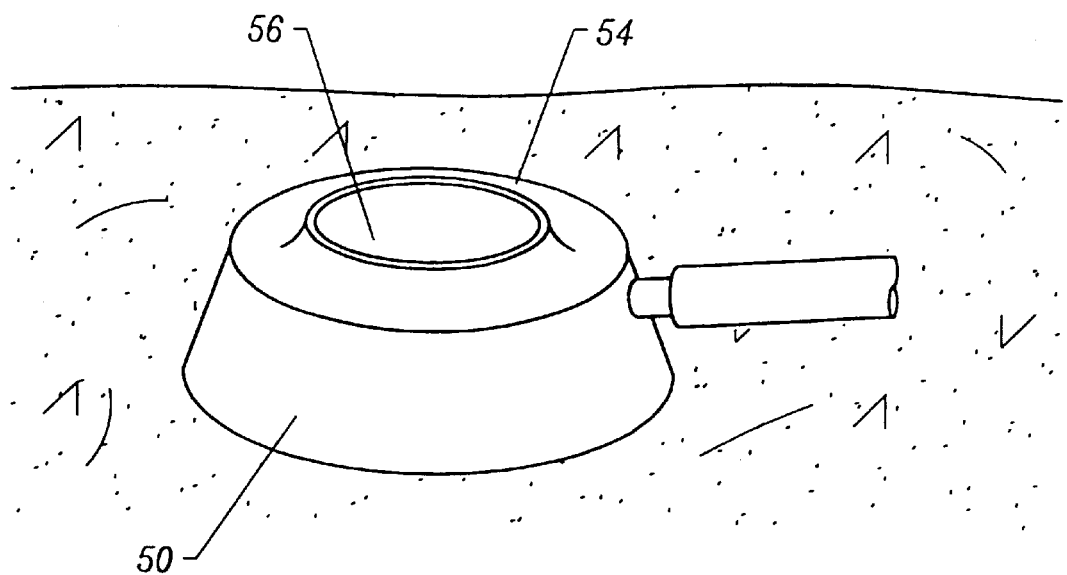
FIG. 3 illustrates an implanted port which has been modified to facilitate disinfection according to the methods of the present invention.
Figure 4:
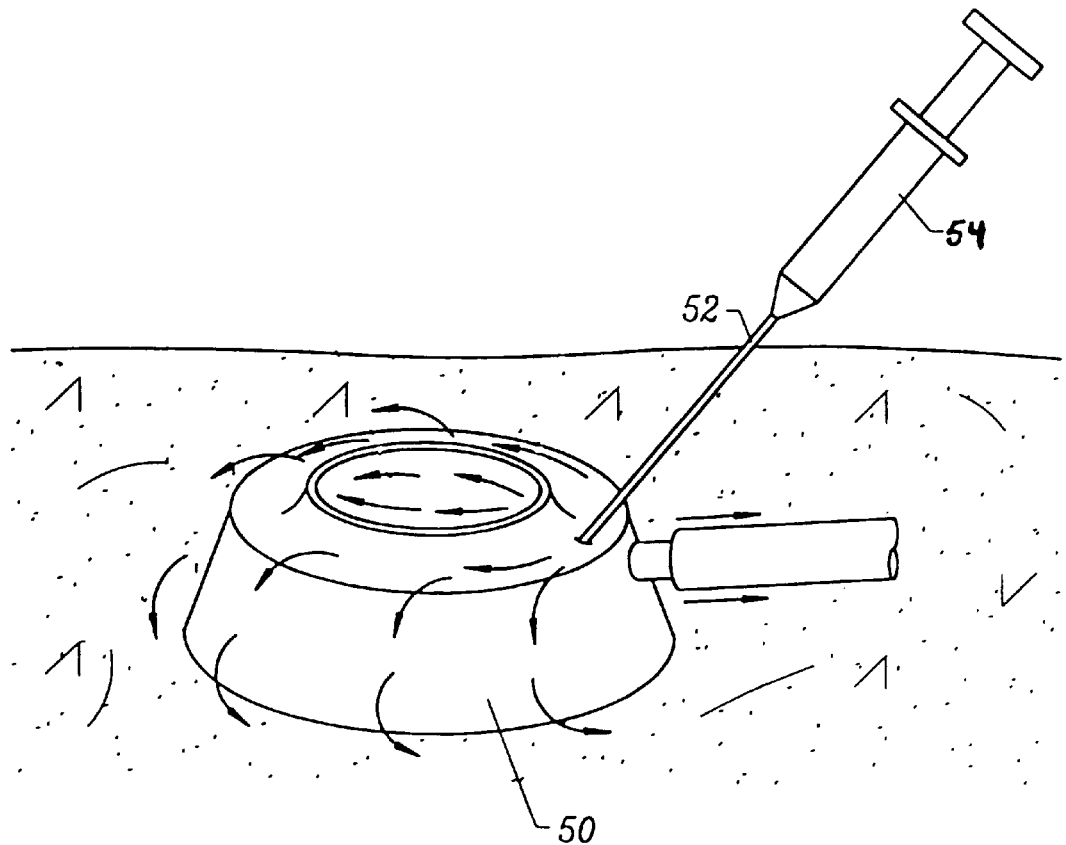
FIG. 4 illustrates a port of FIG. 3 undergoing such disinfection.

The disinfecting methods of the present invention are also useful with a wide variety of other implanted devices. For example, as illustrated in FIGS. 3 and 4, a septum-type port 50 may be disinfected by engaging a needle 52 against an exterior surface of the device, and injecting a suitable anti-microbial agent using a syringe 58. Optionally, the port 50 may be modified to have a target site or region 54, which is shown to be in the form of an annular trough formed concentrically about the septum 56. It will be appreciated that many implantable devices have smooth surface which are difficult to contact with a needle and/or silicone rubber or other penetrable surfaces which will be penetrated by any needle used to introduce an anti-microbial agent. By providing a non-penetrable target site, usually being formed of a metal which is harder than the needle to be used, engagement of a needle against the device can be facilitated. Trough structures, such as trough 54, also serve to distribute the agent about at least a portion of the exterior of the device to facilitate and enhance infusion of the agent over all portions of the surrounding tissue pocket.

Figure 5:
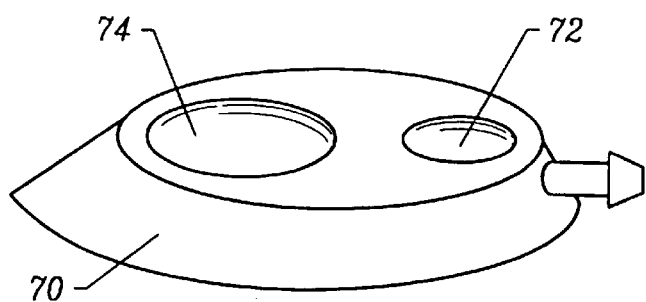
FIG. 5 illustrates an alternative embodiment of an implantable port which has been modified according to the present invention.

An alternative septum-type port 70 having a circular needle target site 72 is illustrated in FIG. 5. In that embodiment, the target is a simple conical indentation in the metallic body of the port 70. The target site 72 is laterally spaced-apart from the septum 74. The treating professional can manually locate a target site 72 and percutaneously access the target site using a needle to introduce the anti-microbial agent in a straightforward manner.

Figure 6:
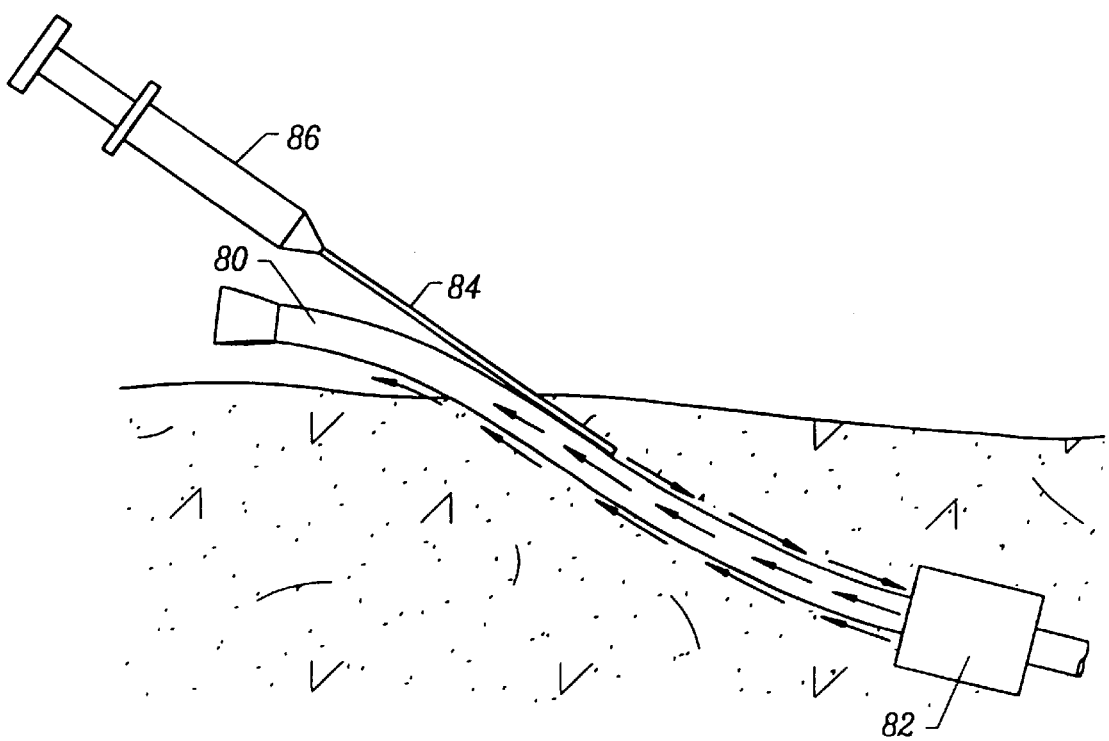
FIG. 6 illustrates a transcutaneously implanted catheter undergoing disinfection according to the method of the present invention.

The methods of the present invention are also suitable for disinfecting transcutaneously implanted devices, such as transcutaneous catheter 80, as illustrated in FIG. 6. Transcutaneous catheters are provided for a variety of purposes, including hemodialysis and peritoneal dialysis access. A free, proximal end of the catheters generally remains accessible above a patient's skin, while a cuff 82 acts as an infection barrier below the skin. While the cuff 82 is generally effective to prevent the progress of an infection down the catheter, there is still a region between the cuff and the skin surface which is subject to infection. The present invention can be used to flush that area with a disinfectant with an anti-microbial agent using a needle 84 and syringe 86, as shown in FIG. 6. The needle 84 is introduced through the percutaneous tissue opening, and the needle tip inserted along the tunnel/tract surrounding the catheter. The syringe 86 is then used to inject the anti-microbial fluid into the tissue pocket until it encounters the implanted cuff 82. Preferably, the needle 84 will be blunt at its tip in order to avoid damage to the catheter. Alternatively, the catheter could be clad with a protective sheath for use with a sharp needle. The anti-microbial agent will thus generally fill and flush the tissue pocket and eventually pass outwardly through the region surrounding the transcutaneous penetration on the patient's skin surface.

Figure 7:
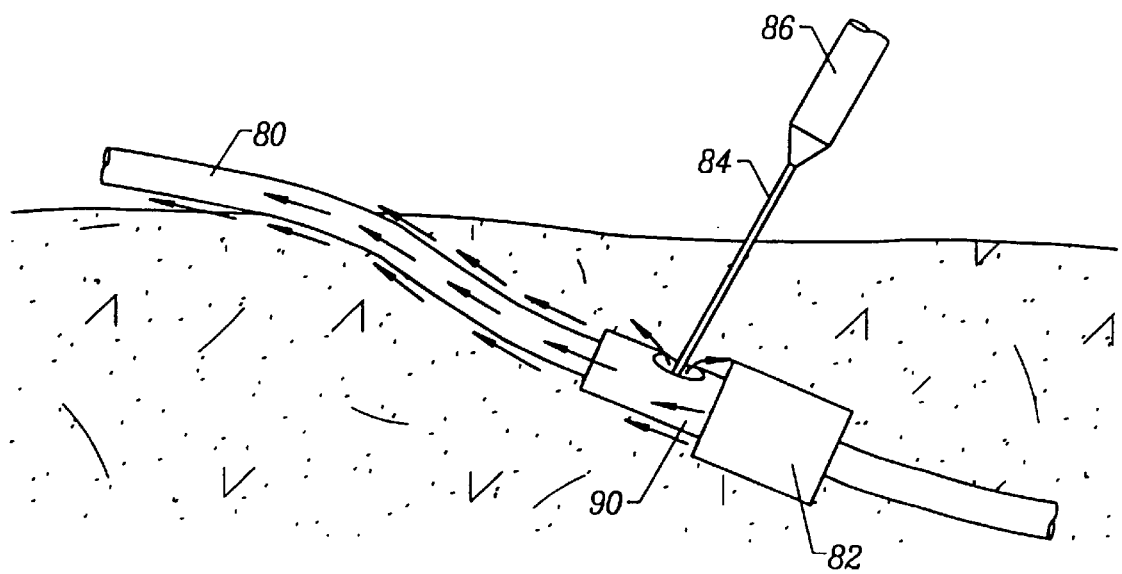
FIG. 7 illustrates a transcutaneously implanted catheter which has been modified to facilitate disinfection according to the methods of the present invention.

Transcutaneous catheters of the type illustrated in FIG. 6 may be improved by providing a hardened target region 90, preferably at a location immediately proximal of the implantable cuff 82, as shown in FIG. 7. The target region may be in the form of a metal sleeve having a conical or other depression designed for receiving the sharpened distal end of needle 84. The needle 84 may then be percutaneously introduced through the skin so that its distal tip engages the target region 90. The disinfectant may then be injected from the region immediately adjacent the implanted cuff 82 so that the agent flows generally outwardly, as illustrated by the arrows of FIG. 7. Such one-way flushing may in some instances provide a more effective disinfecting action.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for inhibiting infection of a device implanted in a tissue pocket, said method comprising percutaneously injecting a liquid anti-microbial agent to the device in an amount having a volume in the range from 1 to 50 ml sufficient to infuse and flush the tissue pocket, wherein the anti-microbial agent is injected against an external surface of the device.

2. A method as in claim 1, wherein the anti-microbial agent is selected from the group consisting of sodium hypochlorite, calcium hypochlorite, sodium oxychlorosone, alcohols, aldehydes, halides, providone iodine, and peroxides.

3. A method as in claim 1, wherein the agent is a liquid injected at a volume in the range from 2 ml to 25.

4. A method as in claim 1, wherein the agent is injected with a syringe through a needle.

5. A method as in claim 1, wherein the device is selected from the group consisting of ports, catheters, and pacemakers.

6. A method as in claim 5, wherein the device is a subcutaneously implanted port having a cannula connected to a blood vessel or other body lumen or cavity.

7. A method as in claim 1, wherein the anti-microbial agent is injected via a needle which is contacted against a target site on the external surface of the device, wherein the target site is harder than a distal tip of the needle.

8. A method as in claim 1, wherein the anti-microbial agent is injected into an internal volume within the device and infuses outwardly from the volume to the region surrounding the device.

9. A method for inhibiting infection of an implanted port which has an aperture for receiving an access tube through a tissue tract, said method comprising subcutaneously injecting a liquid anti-microbial agent into the aperture in an amount having a volume in the range from 1 ml to 50 ml sufficient to at least partly fill said aperture and to overflow from said aperture through a needle positioned in the same tissue tract as the access device, wherein the aperature is sized to mate with an access tube having a preselected size and wherein the anti-microbial fluid is injected with a needle having a size smaller than the preselected size so that the agent may infuse outwardly through the aperature past the needle.

10. A method as in claim 9, wherein the anti-microbial agent is selected from the group consisting of sodium hypochlorite, calcium hypochlorite, sodium oxychlorosone, alcohols, aldehydes, halides, providone iodine, and peroxides.

11. A method as in claim 9, wherein the agent is a liquid injected at a volume in the range from 2 ml to 25 ml.

12. A method as in claim 9, wherein the agent is injected with a syringe.

13. A method as in claim 9, further comprising introducing or withdrawing a fluid through an access tube percutaneously positioned in the aperture.

14. A method as in claim 13, wherein the anti-microbial agent is injected before the fluid is withdrawn or introduced.

15. A method as in claim 13, wherein the anti-microbial agent is injected after the fluid is withdrawn or introduced.

16. A method for inhibiting infection of a device implanted in a tissue pocket, said method comprising percutaneously injecting an anti-microbial agent to the device selected from the group consisting of ports, catheters, and pacemakers in an amount sufficient to infuse and flush the tissue pocket, wherein the anti-microbial agent is injected against an external surface of the device.

17. A method as in claim 16, wherein the anti-microbial agent is selected from the group consisting of sodium hypochlorite, calcium hypochlorite, sodium oxychlorosone, alcohols, aldehydes, halides, providone iodine, peroxides, and the like.

18. A method as in claim 16, wherein the agent is a liquid injected at a volume in the range from 1 ml to 50 ml.

19. A method as in claim 16, wherein the agent is injected with a syringe through a needle.

20. A method as in claim 5, wherein the device is a subcutaneously implanted port having a cannula connected to a blood vessel or other body lumen or cavity.

21. A method as in claim 16, wherein the anti-microbial agent is injected via a needle which is contacted against a target site on the external surface of the device, wherein the target site is harder than a distal tip of the needle.

22. A method as in claim 16, wherein the anti-microbial agent is injected into an internal volume within the device and infuses outwardly from the volume to the region surrounding the device.

23. A method for inhibiting infection of an implanted port which has an aperture for receiving an access tube through a tissue tract, said method comprising subcutaneously injecting an anti-microbial agent into the aperture in an amount sufficient to at least partly fill said aperture and to overflow from said aperture through a needle positioned in the same tissue tract as the access device wherein the anti-microbial fluid is injected with a needle having a size smaller than the preselected size so that the agent may infuse outwardly through the aperture past the needle.

24. A method as in claim 23, wherein the anti-microbial agent is selected from the group consisting of sodium hypochlorite, calcium hypochlorite, sodium oxychlorosone, alcohols, aldehydes, halides, providone iodine, peroxides, and the like.

25. A method as in claim 23, wherein the agent is a liquid injected at a volume in the range from 0.05 ml to 50 ml.

26. A method as in claim 23, wherein the agent is injected with a syringe.

27. A method as in claim 23, further comprising introducing or withdrawing a fluid through an access tube percutaneously positioned in the aperture.

28. A method as in claim 27, wherein the anti-microbial agent is injected before the fluid is withdrawn or introduced.

29. A method as in claim 27, wherein the anti-microbial agent is injected after the fluid is withdrawn or introduced.

30. A method for inhibiting infection of a device implanted in a tissue pocket, said method comprising percutaneously injecting an anti-microbial agent to the device in an amount sufficient to infuse and flush the tissue pocket, wherein the anti-microbial agent is injected against an external surface of the device.

31. A method as in claim 30, wherein the anti-microbial agent is selected from the group consisting of sodium hypochlorite, calcium hypochlorite, sodium oxychlorosone, alcohols, aldehydes, halides, providone iodine, peroxides, and the like.

32. A method as in claim 30, wherein the agent is a liquid injected at a volume in the range from 1 ml to 50 ml.

33. A method as in claim 30, wherein the agent is injected with a syringe through a needle.

34. A method as in claim 30, wherein the device is selected from the group consisting of ports, catheters, and pacemakers.

35. A method as in claim 34, wherein the device is a subcutaneously implanted port having a cannula connected to a blood vessel or other body lumen or cavity.

36. A method as in claim 30, wherein the anti-microbial agent is injected via a needle which is contacted against a target site on the external surface of the device, wherein the target site is harder than a distal tip of the needle.

37. A method as in claim 30, wherein the anti-microbial agent is injected into an internal volume within the device and infuses outwardly from the volume to the region surrounding the device.

* * * * *